United States Patent
Mundell et al.

(10) Patent No.: US 11,083,169 B2
(45) Date of Patent: Aug. 10, 2021

(54) TRAINING APPARATUS AND METHOD FOR FEEDING ANIMALS DURING TRAINING SESSIONS FOR REINFORCEMENT OF BEHAVIORS

(71) Applicant: Companion Labs, Inc., San Francisco, CA (US)

(72) Inventors: Paul Mundell, San Francisco, CA (US); John Honchariw, San Francisco, CA (US)

(73) Assignee: Companion Labs, Inc., San Francisco, CA (US)

( * ) Notice: Subject to any disclaimer, the term of this patent is extended or adjusted under 35 U.S.C. 154(b) by 0 days.

(21) Appl. No.: 17/105,412

(22) Filed: Nov. 25, 2020

(65) Prior Publication Data
US 2021/0153456 A1    May 27, 2021

Related U.S. Application Data

(60) Provisional application No. 62/940,752, filed on Nov. 26, 2019.

(51) Int. Cl.
| | |
|---|---|
| *A01K 5/02* | (2006.01) |
| *A01K 15/02* | (2006.01) |
| *A01K 29/00* | (2006.01) |
| *A61B 5/00* | (2006.01) |

(52) U.S. Cl.
CPC .......... *A01K 5/0275* (2013.01); *A01K 15/021* (2013.01); *A01K 29/005* (2013.01); *A01K 5/0291* (2013.01); *A61B 5/4866* (2013.01); *A61B 2503/40* (2013.01)

(58) Field of Classification Search
CPC ...... A01K 5/02; A01K 5/0225; A01K 5/0275; A01K 15/021; A01K 29/005
See application file for complete search history.

(56) References Cited

U.S. PATENT DOCUMENTS

| | | | | |
|---|---|---|---|---|
| 5,351,653 A | * | 10/1994 | Marischen | A01K 15/021 119/719 |
| 6,651,592 B2 | * | 11/2003 | Maddox | A01K 5/0114 119/712 |
| 7,380,518 B2 | * | 6/2008 | Kates | G01S 1/70 119/72 |

(Continued)

*Primary Examiner* — Michael H Wang
(74) *Attorney, Agent, or Firm* — Run8 Patent Group, LLC; Peter Miller; Leah Raddatz

(57) ABSTRACT

One variation of a method for selectively serving primary reinforcers to an animal includes: accessing a set of characteristics of an animal and estimating a target caloric intake of the animal based on the set of characteristics; identifying a type of primary reinforcer loaded into a training apparatus configured to dispense units of the primary reinforcer based on behaviors performed by the animal responsive to commands output by the training apparatus; in response to identifying the type of primary reinforcer as a first primary reinforcer, loading a first nutrient profile for the first primary reinforcer; and, in response to the first nutrient profile specifying a first caloric density of units of the first primary reinforcer, loading a first training protocol for a first training session for the animal onto the training apparatus based on the target caloric intake of the animal.

19 Claims, 5 Drawing Sheets

(56) References Cited

U.S. PATENT DOCUMENTS

| | | | | |
|---|---|---|---|---|
| 8,633,981 | B2* | 1/2014 | Russoniello | A01K 15/025 |
| | | | | 348/114 |
| 8,944,006 | B2* | 2/2015 | Anderson | A01K 5/00 |
| | | | | 119/51.01 |
| 9,737,049 | B2* | 8/2017 | Trottier | A01K 5/0258 |
| 9,750,229 | B2* | 9/2017 | Stewart | A01K 5/0275 |
| 10,091,972 | B1* | 10/2018 | Jensen | A01K 5/0283 |
| 10,115,110 | B2* | 10/2018 | Gibbs | A01K 5/01 |
| 2010/0095896 | A1* | 4/2010 | Van Wye | A01K 15/02 |
| | | | | 119/57.92 |
| 2010/0263596 | A1* | 10/2010 | Schumann | A01K 5/0283 |
| | | | | 119/51.02 |
| 2011/0139076 | A1* | 6/2011 | Pu | A01K 5/0114 |
| | | | | 119/51.02 |
| 2016/0012748 | A1* | 1/2016 | Donavon | G09B 5/02 |
| | | | | 434/225 |
| 2016/0015004 | A1* | 1/2016 | Bonge, Jr. | A01K 27/006 |
| | | | | 119/718 |
| 2016/0015005 | A1* | 1/2016 | Brown, Jr. | H04L 65/4084 |
| | | | | 340/573.3 |
| 2016/0029592 | A1* | 2/2016 | Springer | A01K 5/02 |
| | | | | 119/51.11 |
| 2016/0192619 | A1* | 7/2016 | Gibbs | A01K 5/00 |
| | | | | 119/61.57 |
| 2016/0374316 | A1* | 12/2016 | Mainini | G06F 3/017 |
| | | | | 119/51.02 |
| 2020/0250733 | A1* | 8/2020 | Hullverson | G06N 3/08 |

* cited by examiner

US 11,083,169 B2

TRAINING APPARATUS AND METHOD FOR FEEDING ANIMALS DURING TRAINING SESSIONS FOR REINFORCEMENT OF BEHAVIORS

CROSS-REFERENCE TO RELATED APPLICATIONS

This Application claims the benefit of U.S. Provisional Application No. 62/940,752, filed on 26 Nov. 2019, which is incorporated in its entirety by this reference.

TECHNICAL FIELD

This invention relates generally to the field of animal training and more specifically to a new and useful method for scheduling and monitoring food consumption during animal training sessions in the field of animal training.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method

As shown in FIGS. 1-5, a method S100 for selectively serving primary reinforcers to an animal includes: at a first time, accessing a set of characteristics of an animal in Block S110 and estimating a target caloric intake of the animal based on the set of characteristics in Block S120; at a second time, identifying a type of primary reinforcer loaded into a training apparatus 100 configured to dispense units of the primary reinforcer based on behaviors performed by the animal responsive to commands output by the training apparatus 100 in Block S130; in response to identifying the type of primary reinforcer as a first primary reinforcer, loading a first nutrient profile for the first primary reinforcer in Block S140; and, in response to the first nutrient profile specifying a first caloric density of units of the first primary reinforcer, loading a first training protocol for a first training session for the animal onto the training apparatus 100 based on the target caloric intake of the animal and the first caloric density of units of the first primary reinforcer in Block S150.

Figure 1:
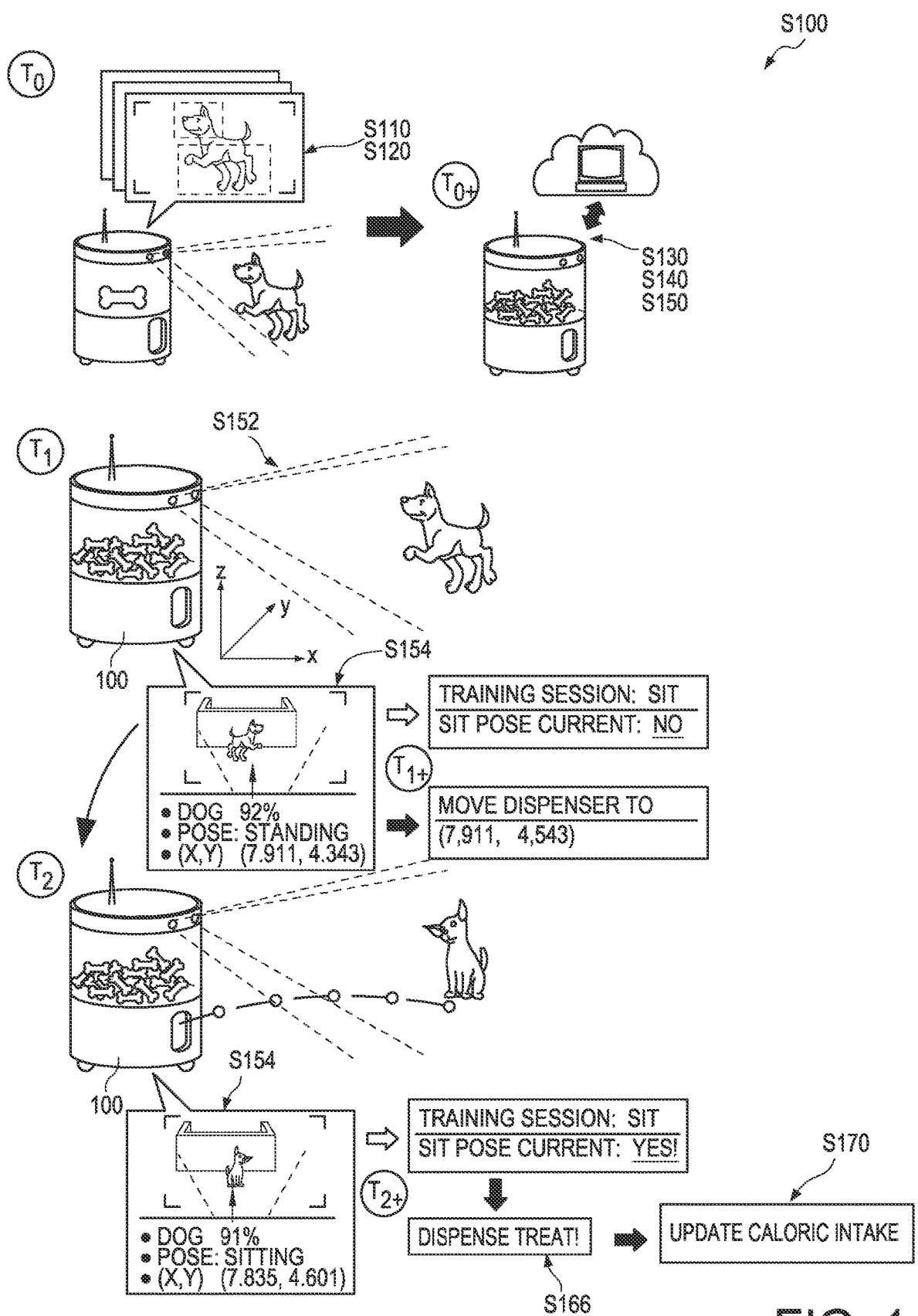
FIG. 1 is a schematic representation of a method.
Figure 2:
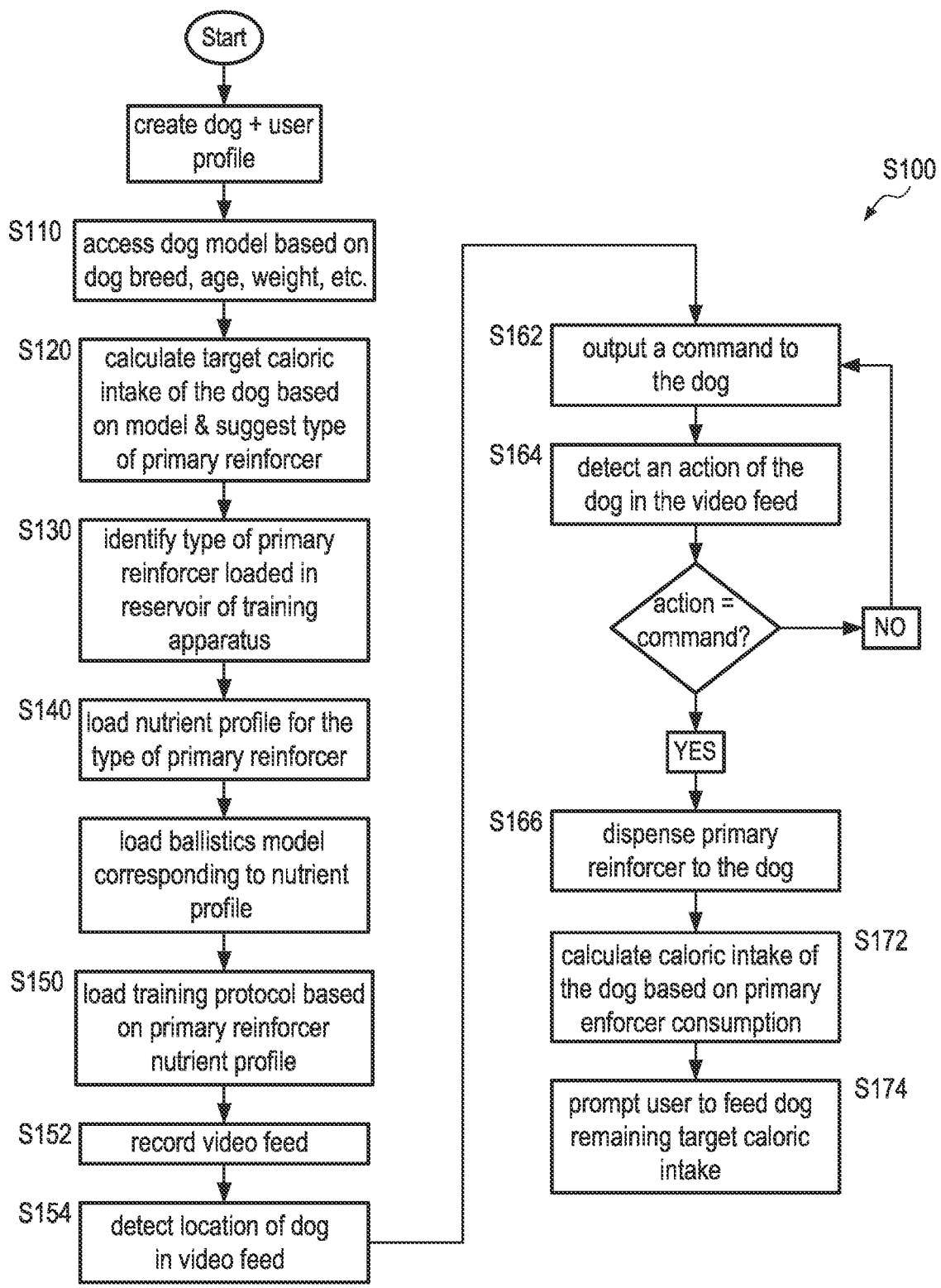
FIG. 2 is a flowchart representation of one variation of the method.
Figure 3:
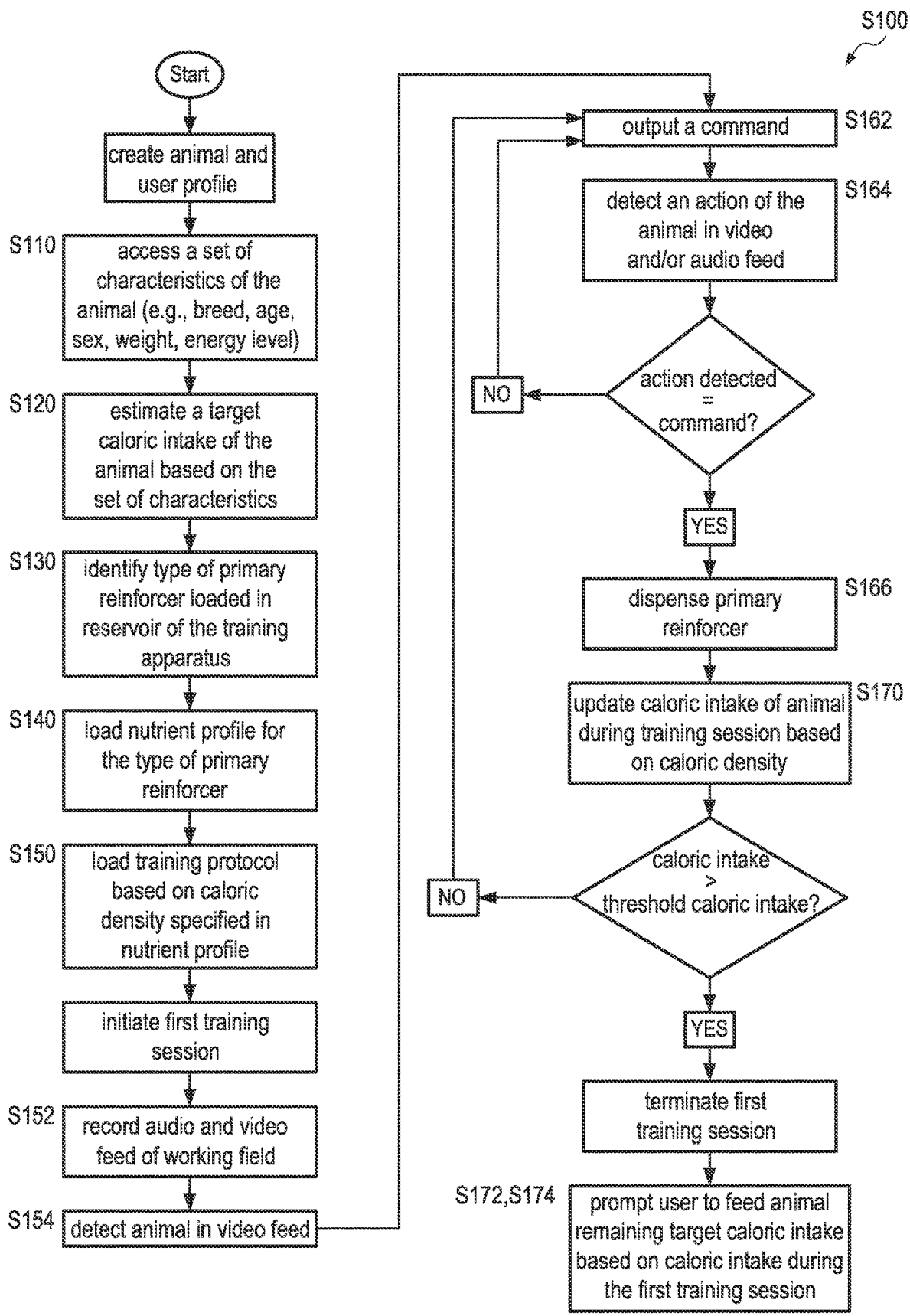
FIG. 3 is a flowchart representation of one variation of the method.
Figure 5:
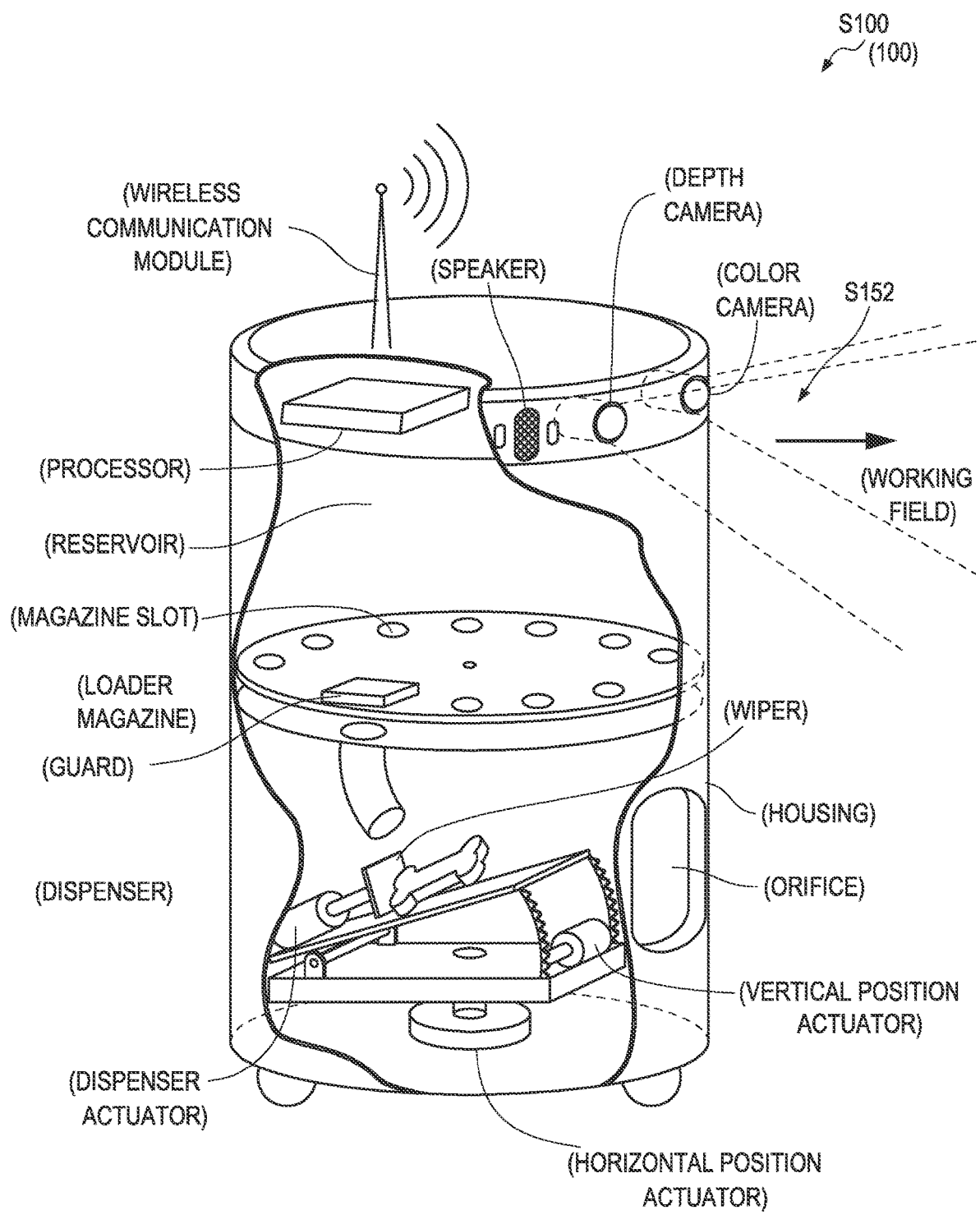
FIG. 5 is a schematic representation of one variation of the method.

As shown in FIGS. 2, 3, and 5, one variation of the method S100 further includes, during the first training session at the training apparatus 100: capturing an audio feed and a video feed of a working field near the training apparatus 100 in Block S152; detecting the animal in the video feed in Block S154; outputting a command in Block S162; detecting an action of the animal in the video feed responsive to the command in Block S164; and dispensing a unit of the primary reinforcer in response to detection of the action corresponding to the command in Block S166.

As shown in FIG. 3, one variation of the method S100 includes, at a first time: accessing a target caloric intake of an animal in Block S120; and identifying a type of primary reinforcer loaded into a training apparatus 100 configured to dispense units of the primary reinforcer based on behaviors performed by the animal responsive to commands output by the training apparatus 100 in Block S130. In this variation, the method S100 further includes, during a first training session: capturing a video feed of a working field near a training apparatus 100 configured to dispense units of a primary reinforcer based on behaviors performed by the animal responsive to commands output by the training apparatus 100 in Block S152; detecting the animal in the video feed in Block S154; and tracking a caloric intake of the animal based on a quantity of units of the primary reinforcer dispensed by the training apparatus 100 in Block S170.

As shown in FIGS. 2 and 3, one variation of the method S100 further includes: calculating a first proportion of the target caloric intake of the animal consumed by the animal during the first training session in Block S172; and prompting the user to feed the animal a second proportion of food based on a difference between the first proportion and the target caloric intake in Block S174.

Figure 4:
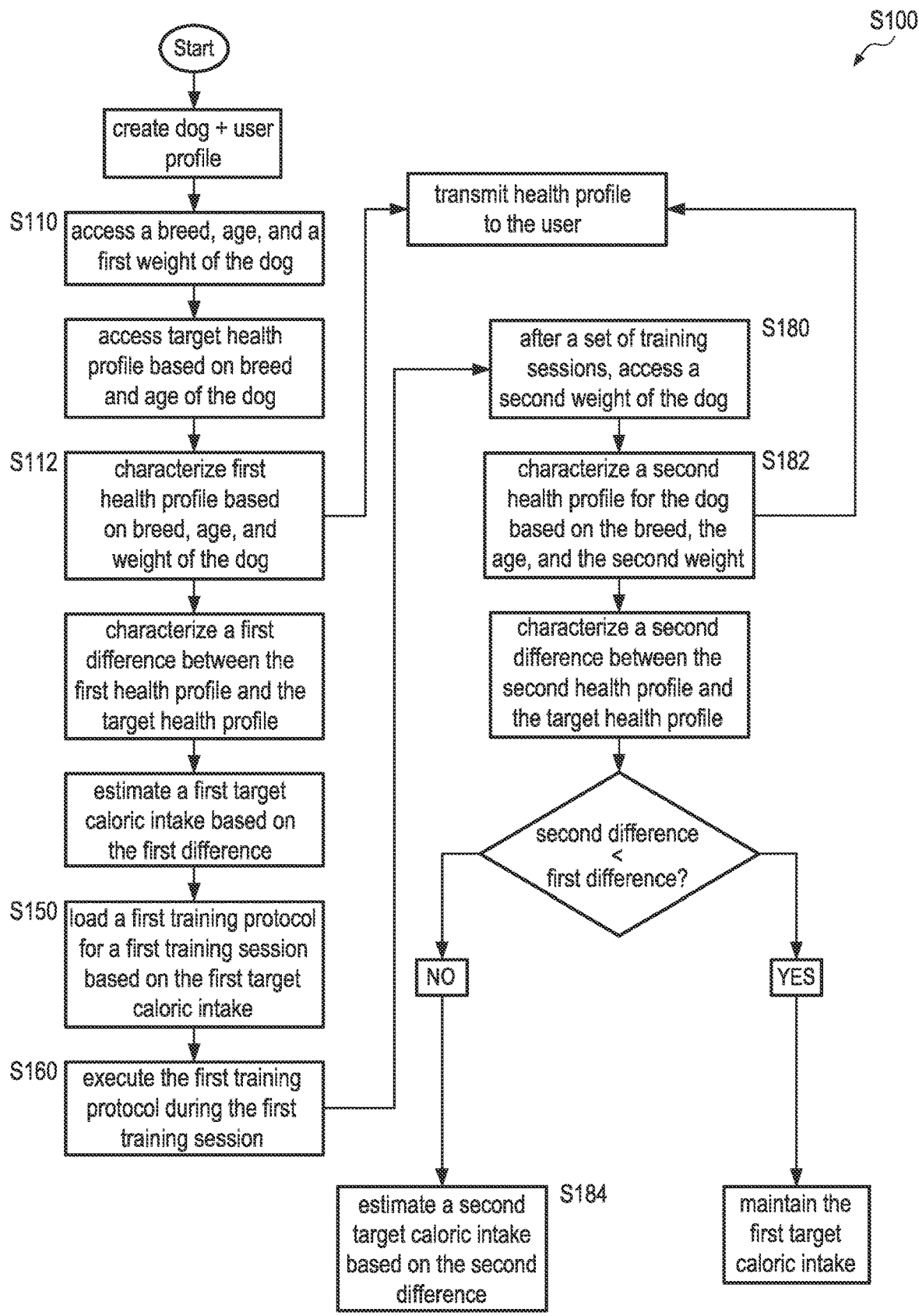
FIG. 4 is a flowchart representation of one variation of the method.

As shown in FIG. 4, one variation of the method S100 includes, during a first period: accessing a first set of characteristics of an animal in Block Silo; characterizing a first health profile of the animal based on the first set of characteristics in Block S112; estimating a first target caloric intake of the animal based on the first health profile in Block S120; and selecting a first training protocol, for a first training session for the animal, for loading onto a training apparatus 100 configured to dispense units of a primary reinforcer based on behaviors performed by the animal responsive to commands output by the training apparatus 100 based on the target caloric intake of the animal in Block S150. The method further includes, during the first training session, succeeding the first period, executing the first training protocol in Block S160. The method further includes, during a second period succeeding the first training session: accessing a second set of characteristics of the animal in Block S180; characterizing a second health profile of the animal based on the second set of characteristics in Block S182; and estimating a second target caloric intake of the animal based on the first health profile and the second health profile in Block S184.

2. Applications

Generally, the method S100 is executed by the training apparatus 100 and/or by a computer system to: suggest and identify a primary reinforcer (e.g., treats, kibble) loaded into the training apparatus 100; to track calories dispensed—in the form of the primary reinforcer—by the training apparatus 100 to a dog during a training session to reinforce actions performed by the dog responsive to commands issued by the training apparatus 100; and to control total dispensations of the primary reinforcer and/or the duration of the training session according to dispensed calories and a caloric need of the dog. The training apparatus 100 and/or the computing device can also return feeding guidance to a user (e.g., the dog's owner; a dog trainer) based on calories dispensed during the training session and the caloric need of the dog, thereby enabling the user to account for the training session when feeding the dog and fulfill the dog's daily nutritional needs while maintaining daily feeding rituals and longer-term health of the dog.

In particular, the training apparatus 100 can execute Blocks of the method S100 to: match a particular type of primary reinforcer to a dog based on characteristics (e.g., age, breed, weight, sex, reproductive status, activity level) of the dog owned; prompt the dog's owner (hereinafter the "user") to retrieve and load this primary reinforcer into an autonomous training apparatus 100 (hereinafter the "training apparatus 100"); schedule a training session for the dog based on these characteristics and the type of primary reinforcer loaded into the training apparatus 100; initiate training sessions for the dog at the training apparatus 100; and define a feeding schedule for the dog based on these characteristics of the dog, the type of primary reinforcer loaded into the training apparatus 100, and the quantity of units of the primary reinforcer dispensed to the dog during this first training session. During the training session, the training apparatus 100 can: capture a video feed of a field around the training apparatus 100; detect the dog in the video feed; capture an audio feed of an area within proximity of the apparatus; detect dog vocalizations in the audio feed; output audible and/or visual commands to the field; interpret the position, pose, and/or action of the dog in this video feed responsive to these commands; and selectively output units of the primary reinforcer to the dog when the training apparatus 100 detects the dog in a position, in a pose, or performing an action associated with these commands in order to reinforce the dog's positive response to these commands and understood connection between these commands and actions. Additionally and/or alternatively, the training apparatus 100 can selectively output units of the primary reinforcer to the dog when the training apparatus 100 responsive to detecting the dog in a position, in a pose, or performing an action unprovoked (e.g., with no command output) in order to positively reinforce this detected behavior. The training apparatus 100 can track both the quantity of these primary reinforcer units dispensed to the dog during this training session and the dog's progress learning this behavior and/or command (e.g., "sit," "stay,", "lie down," "no barking") during this training session.

The training apparatus 100 can also: interpret the dog's size, weight, growth rate, etc. over time based on images (e.g., color images, depth images, and/or point clouds) recorded by the training apparatus 100 (e.g., via a depth camera) over multiple training sessions; estimate whether the dog's caloric needs are currently met (or whether a target proportion of the dog's caloric needs are met) based on these characteristics of the dog and units of the primary reinforcer dispensed to the dog during a current training session; and update the type of primary reinforcer recommended to the user, update the feeding schedule for the dog, and/or update the training schedule according to the dog's responsiveness during training sessions and the dog's caloric needs over time.

In one implementation, the training apparatus 100 initially prompts a user (e.g., at a screen of the training apparatus 100, at the user's mobile phone) to set up a dog profile for the dog (e.g., within a user portal) and to specify characteristics of the dog, such as the dog's breed, age, and/or weight. Based on these characteristics of the dog provided by the user, the training apparatus 100 can select and/or suggest particular primary reinforcers to the user. Over time, the training apparatus 100 can update the dog profile as the dog ages and/or changes in size (e.g., gains weight or loses weight) and update primary reinforcer recommendations for the user accordingly. (Alternatively, the training apparatus 100 can automatically extract these characteristics from an image of the dog uploaded by the user or from an image or video feed recorded by the training apparatus 100 while the dog is occupying the field near the training apparatus 100.)

The training apparatus 100 can then: set a daily caloric intake for a dog based on these characteristics of the dog (e.g., breed, age, weight) captured during initial onboarding of the dog; and allocate a proportion of this daily caloric intake to units of primary reinforcer dispensed by the training apparatus 100 during upcoming training sessions with the dog, such as: 50% by default; proportional to a caloric density of the recommended primary reinforcer; or proportional to a difficulty level of an upcoming training session.

Therefore, the training apparatus 100 can: detect a first primary reinforcer loaded at the training apparatus 100; identify the first primary reinforcer and access a first nutrient profile for the first primary reinforcer; load a first training session based on the nutrient profile of the first primary reinforcer; and execute the first training session including dispensation of units of the first primary reinforcer for reinforcement of actions performed by a dog during the training session. The training apparatus 100 can also: calculate a caloric consumption of the dog during the training session, based on the first nutrient profile and a quantity of units of the primary reinforcer consumed by the dog during the first training session; recommend to the user a volume or weight of food to feed the dog at a next meal based on the caloric consumption of the dog during the first training session; recommend to the user a second primary reinforcer for a next training session based on a weight of the dog, dog expertise, and/or difficulty of the next training session; and, before the next training session, confirm the second primary reinforcer was loaded in the training apparatus 100.

Additionally and/or alternatively, the training apparatus 100 can set and/or modify the proportion of this daily caloric intake allocated to the dog during training based on a rigor or difficulty of an upcoming training session scheduled for the dog or based on the dog's current skill level (e.g., based on the dog's success during past training sessions with the training apparatus 100). For example, the training apparatus 100 can: increase the proportion of this daily caloric intake allocated to the dog on days on which new training sessions or training sessions with high difficulty are scheduled for the dog; and lower the proportion of this daily caloric intake allocated to the dog on days on which training sessions with lower difficulty or previously "mastered" by the dog are scheduled. Therefore, the training apparatus 100 can: autonomously reinforce behaviors of varying difficulty by dispensing units of primary reinforcer to the dog during training sessions; leverage a record of caloric density of these units to prevent over- and underfeeding of the dog during these training sessions and to provide feedback to the dog's owner to prevent over- and underfeeding; and adjust prompts and recommendations for units of primary reinforcer and regular food (e.g., food regularly fed to the dog by the user) for the dog based on training sessions scheduled for the dog, the "quality" (e.g., caloric density) of these units of primary reinforcer, and the dog's training history.

The training apparatus 100 is described below as executing Blocks of the method S100 to autonomously train a dog and to manage caloric consumption by the dog over time. However, the training apparatus 100 can execute these Blocks of the method independently or in conjunction with a local computing device (e.g., a smartphone executing a user portal or a training application) or a remote computer system (e.g., a computer network, a remote server) in order to train any other type of animal, such as a cat, a bird, or a horse.

The training apparatus 100 is described herein as executing the method S100 to train an individual dog—such as at the user's home—and to return food-related prompts to the dog's owner based on caloric consumption by the dog during training sessions at the training apparatus 100. However, the training apparatus 100 can similarly execute the method S100 to train multiple dogs present in the user's home over time and to return food-related prompts for these dogs to the user based on caloric consumption by these dogs during their corresponding training sessions. Additionally or alternatively, the training apparatus 100 can be installed or located at a boarding facility, a training facility, an animal shelter, or other facility, can execute Blocks of the method S100 to train dogs moving through this facility, and can return food-related recommendations to facility staff and/or these dogs' owners based on caloric consumption by these dogs during their corresponding training sessions at the training apparatus 100.

3. Training Apparatus

As shown in FIG. 4, a training apparatus 100 includes: a suite of optical sensors configured to record images (e.g., color and/or depth images) of a working field ahead of the training apparatus 100; audio sensors configured to record ambient noise and animal vocalizations within the working field around the training apparatus 100; a speaker configured to output audible cues; a wireless communication module configured to download data and/or an animal model from a remote database or local computing device; a primary reinforcer reservoir configured to store units of a primary reinforcer, such as loose units or units in a magazine; a dispenser configured to eject units of the primary reinforcer into the working field; a loader configured to load individual units from the reservoir into the dispenser; a processor configured to interpret positions and poses of an animal in the working field in (near) real-time from images recorded by the suite of optical sensors, to move the dispenser into axial alignment with the dog as the dog moves through the working field, and to selectively trigger the dispenser to eject a unit of primary reinforcer toward, near, at, or remotely from the dog; and a housing containing these elements.

In one variation, the training apparatus 100 can be configured to wirelessly communicate (e.g., via the wireless communication module) with a set of secondary devices proximal (e.g., within a user's home) the training apparatus 100. For example, the training apparatus 100 can be configured to wirelessly communicate with a robotic vacuum owned by the user to clean the working field after completion of a training session for the dog. Additionally and/or alternatively, the training apparatus 100 can be configured to trigger activation of the robotic vacuum upon detecting absence of the dog from the working field for a threshold duration. Therefore, in this example, the training apparatus 100 can both enable cleaning of the working field to remove scents and/or physical units of primary reinforcer after a training session while limiting exposure of the dog to the robotic vacuum during and/or immediate after the training session, in order to discourage the dog from associating the training apparatus 100 with the robotic vacuum.

3.1 Reservoir, Loader, & Dispenser

The primary reinforcer reservoir is configured to store many units of a primary reinforcer. For example, the reservoir can include a container configured to store loose units of the primary reinforcer, a removable locking lid, and an outlet port that releases individual units into the loader. The loader is configured to sequentially move individual units out of the reservoir and into the dispenser. In one implementation, the loader includes an auger extending into the output port of the reservoir, terminating over the dispenser, and powered by a loader actuator that rotates the auger to transfer individual units from the reservoir into the dispenser.

In another implementation, the loader includes a magazine arranged inside the reservoir, configured to rotate inside the reservoir when powered by a loader actuator, and defining one or more slots configured to sequentially align with the outlet port in the reservoir. In this implementation, each slot can be sized to accept one unit of the primary reinforcer, and the reservoir can include a guard arranged inside the reservoir over the outlet port and offset from the outlet port by a distance sufficient for the magazine to pass between the guard and the outlet port. To dispense a unit, the loader actuator (e.g., a rotary electric motor) can index the magazine forward by an angular distance between adjacent slots in the magazine, thereby aligning a next slot—currently loaded with a single unit of the primary reinforcer—with the outlet port in the reservoir, which releases this unit from this slot (or "magazine slot") toward the dispenser while the guard prevents additional units of the primary reinforcer from flowing down into this slot and through the outlet port in the reservoir.

(The loader can also include an optical detector or other sensor arranged across the outlet port in the retainer plate and configured to output a signal indicating that a unit has passed through the outlet port and into the dispenser below.)

The dispenser is configured to eject a unit of a primary reinforcer into the field, such as to a target lateral and depth position in the working field to land at an animal's feet or along a target trajectory to land at or near the animal's mouth. Additionally and/or alternatively, the dispenser can be configured to eject a unit of a primary reinforcer within a threshold distance of the dog in the working field to encourage the dog to move from a current position and/or pose.

In one implementation, the dispenser includes: a chamber arranged below the outlet of the loader (e.g., at the output end of the auger-type loader or below the outlet port of the reservoir) and configured to receive individual units of a primary reinforcer from the loader; an orifice or barrel extending from the chamber and facing the working field; a wiper (or a pin) configured to advance and retract behind the chamber; and a dispenser actuator configured to rapidly advance the wiper (or the pin) forward toward the chamber to drive individual units through the orifice and into the working field. For example, the actuator can include a solenoid configured to drive the wiper (or the pin) forward when triggered by the processor. In another example, the wiper (or the pin) is spring loaded; and the dispenser includes a linear or rotary actuator configured to retract the wiper (or pin) and a second actuator configured to release the wiper (or the pin) to drive the wiper forward and thus project an individual unit from the dispenser.

The dispenser (and loader and/or reservoir) can also be mounted on a gimbal configured to pivot (approximately) in the horizontal plane; and the training apparatus 100 can include a horizontal position actuator (e.g., a rotary electric motor) configured to rotate the gimbal in order to sweep the orifice of the dispenser through a range of angular positions—in the horizontal plane—across the working plane, such as to maintain the axis of the dispenser in alignment with an animal detected in the working field. The dispenser can also include an angular position sensor (e.g., an optical encoder, a potentiometer) configured to output an angular position of the gimbal relative to the housing.

However, the training apparatus 100 can include any other mechanisms configured to rapidly eject individual units into the working field when triggered by the processor and configured to sweep an axis of the dispenser horizontally across the working field.

4. Onboarding a New User

The training apparatus 100 can host or interface with a user portal (e.g., via native application or web application)—executing on a user's computing device (e.g., a smartphone, a tablet)—to configure a series of training protocols for a new animal. For example, once the training apparatus 100 is delivered to the user, the user may download the native application to her smartphone and connect her smartphone to the training apparatus 100, such as by: wirelessly pairing her smartphone to the training apparatus 100; scanning a QR code arranged on the training apparatus 100 to register the training apparatus 100 to her smartphone; or by manually entering into the native application a unique code arranged on the training apparatus 100 or product packaging.

Once the training apparatus 100 is registered and connected to the user's smartphone, the user can create a new profile for her dog within the native application and manually populate the new profile with various information, such as: a name; age; breed; size; sex; reproductive status; activity level; energy level; and/or primary colors of the dog's coat (e.g., black for a black Labrador retriever or reddish-brown for a redbone coonhound). This new profile can be stored locally (e.g., on the training apparatus 100) and/or at a remote database (e.g., in the cloud), and the native application can upload these data to the new profile via the Internet.

In one variation, upon purchase of a new training apparatus 100 by a user and before delivery of the training apparatus 100 to the user, the training apparatus 100—via the user portal—can: prompt the user to specify characteristics (e.g., breed, age, sex, weight, activity level) of the user's dog; calculate a target caloric intake for the user's dog based on these characteristics; select a particular primary reinforcer based on the target caloric intake for the user's dog; and ship the new training apparatus 100 and particular primary reinforcer to the user. For example, the training apparatus 100 can: prompt the user—via a web portal accessed by the user at the user's mobile phone—to specify a type of dog food the dog is currently fed; in response to the user specifying a particular type of dog food, retrieve a nutrient profile for the particular type of dog food within a remote database of nutrient profiles. Then, the training apparatus 100 can: prompt the user to specify a breed and an age of the dog; predict a weight of the dog based on the breed and the age specified by the user; calculate a target caloric intake for daily consumption by the dog based on the predicted weight; select a particular primary reinforcer based on the target caloric intake of the dog; and ship the particular primary reinforcer and the training apparatus 100 to the user. Further, the training apparatus 100 can generate a profile for the dog based on this information provided by the user and automatically link this profile to the training apparatus 100 shipped to the user. In this example, once the training apparatus 100 is delivered to the user, the user may download the native application to her smartphone and login to the profile created for her dog. The training apparatus can then automatically wirelessly pair her smartphone to the training apparatus 100.

4.1 Training Apparatus Configuration

The training apparatus 100 can also define a configuration for the training apparatus 100 based on a type of primary reinforcer selected. For example, in response to selecting a particular primary reinforcer, the training apparatus 100 can select a particular magazine for insertion into the training apparatus 100, the particular magazine matched to a size and a shape of units of the particular primary reinforcer. The training apparatus 100, in conjunction with the remote computer system, can ship the particular magazine along with the particular primary reinforcer and the training apparatus 100 to the user. Alternatively, the training apparatus 100 can suggest a set of magazines, each magazine in the set of magazines configured to be inserted into the training apparatus 100 when a corresponding primary reinforcer fitting a specific magazine is loaded into the reservoir of the training apparatus 100.

5. Target Caloric Intake and Allocation

The training apparatus 100 can estimate a target caloric intake for the dog over a set duration (e.g., a 24-hour period) and designate a proportion of the daily caloric intake dedicated to consumption of units of a primary reinforcer based on characteristics of the dog (e.g., as defined by the user). In one variation, the training apparatus 100 can: set a target caloric intake for a dog based on a breed and an age of the dog as specified by a user; select a particular primary reinforcer for the dog based on the breed and the age; allocate a first proportion of the target caloric intake to the particular primary reinforcer fed to the dog by the training apparatus 100; and allocate a second proportion of the target caloric intake to dog food fed to the dog by the user. For example, if a user specifies a 1-year-old Labrador Retriever, the training apparatus 100 can allocate 80% of the dog's target caloric intake to a primary reinforcer and allocate the remaining 20% of the dog's target caloric intake to dog food fed to the dog by a user. In another example, if a user specifies a 10-year-old Labrador Retriever, the training apparatus 100 can allocate 30% of the dog's target caloric intake to the primary reinforcer and the remaining 70% to the dog food provided by the user. Therefore, the training apparatus 100 can select a target caloric intake for a dog based on characteristics input by the user, further leverage this information to estimate proportions of the target caloric intake dedicated to different types of food (e.g., regular dog food and a primary reinforcer).

In another example, in response to a first user specifying an eight-week-old Chihuahua, the training apparatus 100 can: set a target caloric intake by units of a primary reinforcer of 400 Calories-per-day; set a first unit size for units of the primary reinforcer (e.g., 10 millimeter diameter); calculate a first caloric density of units of the primary reinforcer (e.g., 0.20 Calories/kilogram) based on the target caloric intake and the first unit size; and match the user to a first primary reinforcer based on the first unit size and the first caloric density. In response to a second user specifying a five-year-old Great Dane, the training apparatus 100 can: set a target caloric intake by units of the primary reinforcer of 1,250 Calories-per-day; set a second unit size greater than the first unit size (e.g., 20 millimeter diameter); calculate a second caloric density of units greater than the first caloric density (e.g., 0.50 Calories/kilogram) based on the target caloric intake and the first unit size; and select a second primary reinforcer based on the second unit size and the second caloric density. Therefore, the training apparatus 100 can selectively match users and their dogs to different primary reinforcers based on characteristics of the dogs in order to improve responsiveness of the dogs to training sessions performed by the training apparatus 100.

In one variation, the training apparatus 100 can access a food model configured to intake a set of characteristics of the dog and output a target caloric intake for the dog. For example, the training apparatus 100 can prompt the user to input (e.g., via native application executing on the user's mobile device) a set of characteristics of her dog, such as: a breed; age; sex; weight; reproductive status; activity level (e.g., frequency of exercise, types of activities performed by the dog); energy level; etc. The training apparatus can then: receive the set of characteristics from the user; access the food model; and estimate a target caloric intake for the dog based on the model and the set of characteristics. Alternatively, in another example, the training apparatus 100 can extract the set of characteristics from images (e.g., from a video feed collected by the training apparatus 100) of the dog collected during an initial setup period. The training apparatus 100 can then input these characteristics into the food model to estimate the target caloric intake for the dog.

In one variation, the training apparatus 100 can prompt the user (e.g., via a digital screen on the training apparatus 100, via a user portal accessed at the user's mobile device) to specify a type of dog food the user is currently feeding her dog. For example, the training apparatus 100 can: prompt the user to specify a type of dog food the user currently feeds her dog; access a nutrient profile (e.g., at a remote database) for the type of dog food specified by the user; in response to the nutrient profile specifying a particular caloric density: and generate a feeding schedule for the user specifying a quantity of food to serve her dog and a frequency at which to serve the quantity of food. The training apparatus 100 can generate a feeding schedule prompting the user to serve a first proportion of dog food at a first time and to serve a second proportion of dog food at a second time succeeding the first time by approximately 8 hours (e.g., 2 hours).

5.1 Health Profile

In one variation, the training apparatus 100 can characterize health of the dog based on a set of characteristics of the animal, such as extracted from images of the dog captured during previous training sessions or collected from a survey completed by the user when onboarding the dog to the training apparatus 100. In particular, the training apparatus 100 can: access a set of characteristics of a dog (e.g., input by the user, extracted via images of the animal); and characterize a health profile for the dog based on this set of characteristics. The training apparatus 100 can then leverage this health profile to estimate a target caloric intake (e.g., daily) for the dog.

For example, the training apparatus 100 can prompt the user to input a breed, a sex, an age, an activity level (e.g., average daily exercise), and a weight of her dog when first onboarding the dog to the training apparatus 100 and before a first training session between the dog and the training apparatus 100. Based on these characteristics, the training apparatus 100 can characterize a health profile of the dog. Further, based on the breed, the sex, and the age, the training apparatus 100 can access a target health profile, in a set of target health profiles, for the dog. The training apparatus 100 can then characterize a difference between the health profile of the dog and the target health profile corresponding to the breed, sex, and age. Based on this difference, the training apparatus 100 can estimate a target caloric intake of the dog. In particular, in this example, in response to the target health profile specifying a target weight less than the weight of the dog, the training apparatus 100 can estimate a target caloric intake configured to reduce the weight of the dog toward the target weight. Therefore, in this example, the training apparatus 100 can estimate target caloric intake for the dog based on differences between the dog's current health profile and a target health profile for the dog, in order to drive the dog's health profile toward the target health profile.

In another example, the training apparatus 100 can prompt the user to input a breed, a sex, and an age of her dog. Based on these characteristics, the training apparatus 100 can access a target health profile for the dog corresponding to a healthy dog exhibiting similar characteristics. Further, the training apparatus 100 can access an image of the dog (e.g., recorded by the training apparatus) to estimate additional characteristics of the dog, such as a weight, a size, and/or a shape of the dog. In particular, in this example, the training apparatus 100 can access an image of the dog to estimate a first weight of the dog. Then, in response to the target health profile of the dog specifying a target weight less than the first weight, the training apparatus 100 can estimate a target caloric intake for the dog configured to reduce the dog's weight over time from the first weight to the target weight.

6. Initial Loading of the Training Apparatus

Once the user has received a training apparatus 100 and a particular primary reinforcer, the training apparatus 100 can confirm an identity of the particular primary reinforcer. For example, once a user receives a training apparatus 100 and a primary reinforcer, the training apparatus 100 can prompt the user to: select a type of primary reinforcer within a native application operating on the user's mobile device; scan a SKU value, bar code, or QR code located on packaging of the primary reinforcer via the user's mobile device; and/or scan the SKU value, bar code, or QR code via a scanning device (e.g., the camera or a separate barcode scanner) in the training apparatus 100.

Alternatively, to identify a type of primary reinforcer in the reservoir, the training apparatus 100 can: access a user's purchase history through a web portal to identify a type of primary reinforcer purchased by the user; and/or scan an RFID chip inserted in a unit of the primary reinforcer located in the reservoir.

Upon identification of a first primary reinforcer, the training apparatus 100 can prompt the user to load a first quantity (e.g., a bag of the primary reinforcer, 2 cups of the primary reinforcer, fill threshold reservoir) of the first primary reinforcer into the reservoir. For example, the training apparatus 100 can: prompt the user to scan a SKU included in packaging for primary reinforcers; identify a first primary reinforcer based on the SKU; unlock a lid of a reservoir configured to be filled with primary reinforcers; and prompt the user to pour an entire bag of the first primary reinforcer into the reservoir of the training apparatus 100.

In one variation, the training apparatus 100 can access a nutrient profile of the primary reinforcer and prompt the user to load a particular quantity of the primary reinforcer based on the nutrient profile. For example, the training apparatus 100 can: identify a first primary reinforcer; access a nutrient profile for the first primary reinforcer; and, in response to the nutrient profile for the first primary reinforcer specifying a low caloric density of units of the first primary reinforcer, prompt the user to load a relatively large quantity of the first primary reinforcer.

In one variation, the training apparatus 100 can access a scheduled training session for this particular day, and prompt the user to load a particular quantity of a primary reinforcer based on a rigor of the scheduled training session. For example, on a first day of training for a dog, the training apparatus 100 can: access a training schedule for the dog; in response to the training schedule specifying a low difficulty training session for the dog on the first day of training, prompt the user to load a first quantity of the particular primary reinforcer. Then, on a second day of training for the dog, the training apparatus 100 can: access the training schedule; and, in response to the training schedule specifying a high difficulty training session on the second day of training, prompt the user to load a second quantity of the particular primary reinforcer, the second quantity greater than the first quantity.

In one variation, the training apparatus 100 can implement a counter to track a quantity of units of a particular primary reinforcer available for dispensation. For example, the training apparatus 100 can: identify a first primary reinforcer loaded in the reservoir; access a first nutrient profile of the first primary reinforcer; and, in response to the first nutrient profile specifying a first unit count of 500 units in the first primary reinforcer, update a counter associated with the user to 500 units, thereby enabling dispensation of 500 units of the first primary reinforcer. At a later time, after dispensing 400 units of the first primary reinforcer, in response to detecting a second primary reinforcer in the reservoir, the training apparatus 100 can: identify the second primary reinforcer and access a second nutrient profile for the second primary reinforcer; in response to the second primary reinforcer profile specifying a second unit count of 300, update the counter to include an additional 300 units; and enable dispensation of 400 units (e.g., 100 units of the first primary reinforcer and 300 units of the second primary reinforcer).

In response to the counter reaching zero, the training apparatus 100 can: disable dispensation of units of the primary reinforcer until additional units of the primary reinforcer are identified and loaded into the dispenser. In one variation, the training apparatus 100 can enable dispensations of a limited quantity of substitute units, such that a user may continue dog training during a leeway period for purchasing or receiving a new primary reinforcer. For example, in response to the counter reaching zero, the training apparatus 100 can: prompt a user to purchase or load a new primary reinforcer; and enable dispensation of 20 additional units, such that a user may load a substitute primary reinforcer into the dispenser until the new primary reinforcer is received by the user.

In one variation, after identifying a particular primary reinforcer, the training apparatus 100 can load a ballistics model and/or agitation model corresponding to the particular primary reinforcer. Additionally, the training apparatus 100 can load a corresponding floor model to account for friction and "bounce coefficients" of the particular primary reinforcer with the floor. For example, in response to identifying a particular primary reinforcer, the training apparatus 100 can: access a nutrient profile for units of the particular primary reinforcer; record a size and a shape of units of the particular primary reinforcer as specified in the nutrient profile; access a first agitation model based on a density of units of the first primary reinforcer as specified in the nutrient profile for agitating units in the reservoir of the training apparatus 100; access a first ballistics model based on a size and a shape of units of the first primary reinforcer as specified in the nutrient profile for modelling dispensation of units of the primary reinforcer to the dog; and access a first floor model corresponding to the primary reinforcer for modelling trajectory of units of the primary reinforce upon contact with a floor after dispensation. Then, the training apparatus 100 can mix and dispense units of the primary reinforcer, such that one unit is dispensed at a time and such that each unit reaches a target destination within a target time frame.

7. Training Session

The method S100 includes, during the first training session at the training apparatus 100: capturing a video feed of a field near the training apparatus 100; detecting the dog in the video feed; outputting a command; detecting an action of the dog in the video feed responsive to the command; and dispensing a unit of the primary reinforcer in response to detection of the action corresponding to the command. Generally, the training apparatus 100 can execute methods and techniques described in U.S. patent application Ser. No. 16/418,596, filed on 21 May 2019, which is incorporated in its entirety by this reference.

In one implementation, once a primary reinforcer is loaded in the reservoir of the training apparatus 100, the training apparatus 100 can enable initiation of a training session. For example, the training apparatus 100 can: identify a first primary reinforcer; unlock a reservoir of the training apparatus 100 configured to receive a portion of the primary reinforcer loaded by the user; and, in response to the user loading the reservoir with a portion of the primary reinforcer, enable initiation of a first training session. Once the training apparatus 100 has enabled initiation of the first training session, the training apparatus 100 can initiate the first training session at a scheduled time (e.g., immediately following loading of the reservoir, at 9:00 AM each day, at 5:00 PM each day). At the scheduled time, the training apparatus 100 can initiate and perform a first training session. During the first training session, the training apparatus 100 can instruct a dog to perform specific tasks (e.g., "sit", "stay", "lie down") and, in response to the dog performing these tasks, dispense units of the primary reinforcer in the reservoir to reward the dog.

In one variation, the training apparatus 100 can receive input from the user regarding user preference for a feeding schedule for the user's dog. For example, a user may prefer to personally feed her dog in the morning and schedule the training apparatus 100 for training sessions in the evening. In this example, the training apparatus 100 can: prompt the user to input a set of user preferences including feeding schedule preference; in response to the user inputting a feeding schedule preference of personally feeding her dog a first feeding at 8:00 am each day, schedule training sessions for six to ten hours offset the first feeding; and initiate a first training session at 5:00 pm.

In one variation, the training apparatus 100 can access a ballistics model to update a training apparatus 100 configuration for different primary reinforcers. For example, the training apparatus 100 can: identify a type of primary reinforcer loaded in the reservoir of the training apparatus 100; access a nutrient profile for the type of primary reinforcer identified; extract a size, weight, and shape of units of the primary reinforcer from the nutrient profile; identify an agitation profile for units of the primary reinforcer based on the size and shape of units of the primary reinforcer; identify a ballistics model for units of the primary reinforcer based on the weight and shape of units of the primary reinforcer; agitate the primary reinforcer according to the agitation profile such that units of varying size and composition are evenly distributed throughout the primary reinforcer; oscillate a magazine in the training apparatus 100 according to the agitation profile such that one unit is dispensed each oscillation; catapult units at a first force according to the ballistics model such that units land at a target location when dispensed.

In one variation, the training apparatus 100 can update the agitation profile and the ballistics model based on the moisture content of units of the primary reinforcer. For example, if a user receives a new primary reinforcer and loads the new primary reinforcer in the reservoir the same day the new primary reinforcer is received, the moisture content for this particular primary reinforcer may be relatively high. However, if the user has previously loaded a first portion of a particular primary reinforcer in the reservoir and now loads a second portion of the particular primary reinforcer, the training apparatus 100 can identify that the user has previously loaded units from this particular primary reinforcer and account for a higher moisture content of units in the second portion than the first portion and update the agitation profile and ballistics model for this particular primary reinforcer.

7.1 Tracking Caloric Intake

In one variation, the training apparatus 100 can track the caloric intake of the dog throughout the training session. In particular, the training apparatus 100 can track a quantity of units of primary reinforcer dispensed throughout the training session. The training apparatus 100 can then estimate a caloric intake of the dog based on a quantity of units of the primary reinforcer dispensed by the training apparatus 100 and the caloric density of units of the primary reinforcer.

For example, during an initial period preceding a training session for a dog, the training apparatus 100 can: identify a type of primary reinforcer loaded into the training apparatus 100; and, in response to identifying the type of primary reinforcer as a first primary reinforcer, load a first nutrient profile for the first primary reinforcer, the first nutrient profile specifying a first caloric density of units of the first primary reinforcer. Then, during the training session, the training apparatus 100 can: record a video feed of a working field near the training apparatus 100; dispense a first unit of the first primary reinforcer based on a behavior performed by the dog responsive to a command output by the training apparatus 100; update a count representative of a quantity of units of the first primary reinforcer dispensed; and update a caloric intake of the dog during the training session based on the count and the first caloric density.

Additionally and/or alternatively, during the training session, the training apparatus 100 can track a quantity of units of the first primary reinforcer physically consumed by the dog. In particular, the training apparatus can confirm whether the dog consumed a unit of the primary reinforcer dispensed by the training apparatus via the video feed. For example, during a training session, the training apparatus 100 can: detect and track the dog's mouth (or nose, snout, or head) in color and/or depth images recorded by the training apparatus 100 after ejecting a unit of a primary reinforcer into the field; detect and track a ground plane in these images; detect and track a location of the unit of the primary reinforcer on the ground plane in these images; and, in response to detecting intersection of the dog's nose with the location on the ground plane in these images, confirm consumption of the unit of the primary reinforcer by the dog. Then, in response to confirming consumption of the unit of the primary reinforcer by the dog, the training apparatus can update the caloric intake of the dog during this training session. Alternatively, in response to detecting no intersection of the dog's nose with the location on the ground plane, the training apparatus can confirm rejection of this unit of primary reinforcer by the dog and therefore exclude this unit of the primary reinforcer from the caloric intake of the dog during the training session.

7.1.1 Real-time Modification of Training Protocol

In one variation, the training apparatus 100 can adjust the training protocol during the training session (e.g., in real time) based on the current caloric intake of the dog in order to reach a particular caloric intake for the dog before an end of the training session. For example, the training apparatus 100 can load a first training protocol for the first training session for a dog, the first training protocol specifying: a target caloric intake for the dog during the training session; and a quantity of dispensations of primary reinforcer, each dispensation corresponding to a particular training instance, in a set of training instances spanning a duration of the training session. However, for a first training instance during the training session, in response to detecting an incorrect behavior (e.g., no change in behavior) performed by the dog responsive to a first command, the training apparatus 100 can withhold a first dispensation of units of primary reinforcer corresponding to the first training instance. After the first training instance, the training apparatus 100 can update the caloric intake of the dog during the training session, the caloric intake exhibiting no change. Therefore, in order to achieve the target caloric intake specified for the training session for the dog, the training apparatus 100 can update the first training protocol to increase the quantity of training instances in the training session, such that the quantity of dispensations within the training session does not change. Additionally and/or alternatively, the training apparatus 100 can update the first training protocol to increase a quantity of units of primary reinforcer included in each remaining dispensation. Thus, the training apparatus 100 can adjust a training protocol loaded onto the training apparatus 100 in real-time based on the caloric intake of the dog during the training session, in order to achieve a particular caloric intake for the dog at an end of the training session.

7.2 Terminating the Training Session

In one variation, the training apparatus 100 can terminate a training session based on the caloric intake of the dog during the training session. In particular, the training apparatus 100 can: track the caloric intake of the dog throughout a training session; and, in response to the caloric intake exceeding a threshold caloric intake, terminate the training session.

For example, prior to initiating a first training session, the training apparatus 100 can: set a threshold caloric intake for the animal during the first training session; access a first caloric density of units of a first primary reinforcer loaded in the training apparatus 100 for dispensation during the first training session; and estimate a threshold quantity of units of the first primary reinforcer for dispensation during the first training session based on the first caloric density and the threshold caloric intake. Then, in response to the quantity of the first primary reinforcer dispensed by the training apparatus 100 exceeding the threshold quantity of units of the first primary reinforcer during the first training session, the training apparatus 100 can terminate the first training session.

In one implementation, the training apparatus 100 can calculate a threshold caloric intake for the training session based on the target caloric intake of the dog. For example, the training apparatus 100 can default to setting the threshold caloric intake at fifty percent of the target caloric intake of the dog. Therefore, in this example, for a dog assigned a target caloric intake of 600 Calories, the training apparatus 100 can calculate a threshold caloric intake of 300 Calories for a training session for this dog. Thus, in response to the caloric intake of this dog exceeding 300 Calories during the training session, the training apparatus 100 can automatically terminate the training session.

Alternatively, in another example, the training apparatus 100 can calculate the threshold caloric intake for a training session based on a set of user preferences input by the user prior to the training session, the set of user preferences including a proportion of the target caloric intake for the dog fed by the user to the dog outside of the training session. In this example, the training apparatus 100 can: access the target caloric intake for the dog; access the set of user preferences; and, in response to the set of user preferences specifying that the user plans to directly feed the dog thirty percent of the target caloric intake over a set duration (e.g. 24 hours), calculate a threshold caloric intake for the training session corresponding to seventy percent of the target caloric intake. Alternatively, if the training apparatus 100 schedules multiple training sessions for a dog within the set duration, the training apparatus 100 can reduce a threshold caloric intake for each training session within the set duration such that a total of each threshold caloric intake corresponds to seventy percent of the target caloric intake.

In one implementation, the training apparatus 100 can terminate a training session after a set duration (e.g., 15 minutes, 30 minutes, 1-hour). For example, the training apparatus 100 can load a particular training protocol, onto the training apparatus 100, specifying a set duration. At the start of the training session, the training apparatus 100 can initiate a timer for the set duration. In response to expiration of the timer, the training apparatus 100 can terminate the training session. In yet another variation, the training apparatus 100 can terminate a training session upon completion of the training protocol loaded for the training session.

8. Completion of the Training Session

Upon completion of the first training session, the training apparatus 100 can record a quantity of units of the primary reinforcer served to the dog and record this quantity to the dog's (e.g., the user's) profile.

In one variation, the training apparatus 100 can calculate a caloric consumption of the dog based on the type of primary reinforcer and the quantity of units in the primary reinforcer served to the dog during the training session. The training apparatus 100 can record the caloric consumption for the training session to the dog profile for this dog.

In one variation, the training apparatus 100 can calculate a caloric consumption for the dog during the training session, and prompt the user to feed the dog an additional quantity of food based on the caloric consumption of the dog during the training session and the dog's target daily caloric intake. For example, the training apparatus 100 can: terminate a training session; calculate a caloric consumption by the dog during the training session based on a quantity of units dispensed during the training session and a caloric density of units; record this calorie consumption to a dog profile within a web portal accessible via the user's mobile device; and, in response to dispensing 50% of a target caloric intake for the dog (e.g., for a 24-hour period), prompt the user to serve the dog a remaining 50% of the target caloric intake.

In another example, for a dog with a target caloric intake of 600 Calories, the training apparatus 100 can: terminate a training session for the dog; in response to dispensing units equivalent to a caloric intake of 300 Calories, calculate a remaining caloric intake of 300 Calories; access a nutrient profile for a type of dog food specified by the owner to extract a caloric density of the dog food; calculate a weight of dog food to be fed to the dog by the user based on the remaining intake and the caloric density of the dog food; and prompt the user to feed the dog the weight of dog food at a time offset from a termination of the training session.

In one variation, the training apparatus 100 can prompt the user to feed the dog at a particular time. For example, the training apparatus 100 can, at a time offset from the termination of a training session by 8 hours, send the user a text message on a mobile device of the user, prompting the user to feed the dog a remainder of the target calorie intake.

In one variation, the training apparatus 100 can prompt the user to feed the dog based on the user's location. For example, the training apparatus 100 can send a notification to the user—via a mobile application accessible on the user's mobile device—when the user is located at her house, the notification specifying to feed the dog the remainder of the target calorie intake at a particular time.

In one variation, the training apparatus 100 can generate a report summarizing the training session and deliver this report to the user. The report can include information such as: a quantity of units of the primary reinforcer dispensed during the training session; a caloric intake of the dog during the training session; a quantity of the target caloric intake remaining after the training session; a suggestion for a type of primary reinforcer to purchase for an upcoming training session; a summary of the dog's behavior during the training session; etc. The training apparatus 100 can generate and deliver this report to the user after each training session. Alternatively, the training apparatus 100 can deliver this report to the user at a set interval (e.g., once per day, once per week) and/or according to a user preference input by the user.

9. Alternate Primary Reinforcer Profiles

In one variation, the training apparatus 100 can prompt the user to purchase a particular type of primary reinforcer based on a rigor of scheduled training sessions. For example, the training apparatus 100 can: at a first time, prompt the user to purchase a first type of primary reinforcer for a first month of training based on a relatively low difficulty level of training sessions during the first month; and, at a second time, prompt the user to purchase a second type of primary reinforcer for a second month of training based on a relatively high difficulty level of training sessions during the first month.

In one variation, the training apparatus 100 can initially identify multiple primary reinforcers to dispense to the dog during different training sessions based on varying rigor of training sessions scheduled for the dog over a first period of time and then supply or recommend these primary reinforcers to the user. For example, the training apparatus 100 can: on a first day, load a first training session specifying a low difficulty level; and prompt the user to load the reservoir of the training apparatus 100 with a first primary reinforcer with units exhibiting a first caloric density. Later, the training apparatus 100 can: on a second day, load a second training session specifying a high difficulty level; and prompt the user to load the reservoir with a second primary reinforcer with units exhibiting a second caloric density greater than the first caloric density. Therefore, the training apparatus 100 can dispense units with higher caloric densities during training sessions of relatively higher difficulty and dispense units with lower caloric densities during easier training sessions. The training apparatus 100 can verify that the user loaded the correct primary reinforcer for the loaded training session before initiating a training session. In response to the user loading a different primary reinforcer than prompted, the training apparatus 100 can select a different training session for that day, and return the loaded training session to a queue.

In one variation, the training apparatus 100 can select a first training session from a queue of training sessions for a particular day based on the primary reinforcer loaded in the reservoir by the user. In this variation, in response to the user loading a particular primary reinforcer into the reservoir, the training apparatus 100 can: access a nutrient profile for the particular primary reinforcer; extract the caloric density of units in the particular primary reinforcer from the nutrient profile; access a queue of training sessions available for this dog on this day; and select a particular training session from the queue based on the caloric density of units in the primary reinforcer loaded in the reservoir. For example, the training apparatus 100 can: identify a particular primary reinforcer loaded into the reservoir of the training apparatus 100; and access a nutrient profile for the particular primary reinforcer specifying a caloric density of 3000 Calories/kilogram. Then, the training apparatus 100 can access a queue of three training sessions available for the user's dog on this particular day, including: a first training session specifying a high level of difficulty and a suggested caloric density of 4000 Calories/kilogram; a second training session specifying a moderate level of difficulty and a suggested caloric density of 3250 Calories/kilogram; and a third training session specifying a low level of difficulty and a suggested caloric density of 2500 Calories/kilogram. In response to the caloric density of units in the particular primary reinforcer exhibiting a caloric density of 3000 Calories/kilogram, the training apparatus 100 can select the second training session for the user's dog for this particular day. Additionally, before initiating a selected training session, the training apparatus 100 can identify a quantity of the particular primary reinforcer available for dispensation (e.g., loaded in the reservoir by a user) during the selected training session and set a training session duration for the selected training session based on the quantity of particular primary reinforcer and/or the caloric density as specified in the nutrient profile. For example, the training apparatus 100 can identify a particular primary reinforcer loaded in the reservoir corresponding to a first caloric density and select a first training session based on the first caloric density. Then, in response to identifying a quantity of 50 units of the particular primary reinforcer loaded in the reservoir, the training apparatus 100 can calculate a duration of 30 minutes for the first training session based on the 50 units of the particular primary reinforcer available for dispensation and the first caloric density.

In one variation, the training apparatus 100 can prompt the user to acquire (e.g., purchase) a particular type of primary reinforcer based on characteristics of the dog, such as: weight; reproductive status; sex; activity level; energy level; etc. The training apparatus 100 can monitor and/or update these characteristics over time to suggest different types of primary reinforcer to the user as her dog progresses through training. In addition, the training apparatus 100 can leverage both rigor of scheduled training sessions and these characteristics of the dog to suggest a particular type of primary reinforcer for the dog to the user.

In one variation, the training apparatus 100 can access a food model configured to intake a set of characteristics of the dog and output a target food profile for the dog. In particular, the training apparatus 100 can leverage characteristics (e.g., breed, age, size, sex, activity level) of a dog to estimate a target food profile for this dog specifying a set of food characteristics such as: caloric density; size of units of the primary reinforcer; texture (e.g., crunchy, soft); ingredients and/or nutrients; etc. For example, the training apparatus can prompt a user to input a breed and an age of her dog. In response to the user specifying a 12-year-old Sheltie, the training apparatus 100 can access the food model to estimate a target food profile for the dog specifying a softer texture, a lower caloric density, and a smaller size of units of the primary reinforcer. Alternatively, in response to the user specifying a 2-year old Golden Retriever, the training apparatus 100 can access the food model to estimate a target food profile for the dog specifying a harder texture, a higher caloric density, and a larger size of units of the primary reinforcer. After estimating the target food profile for the dog, the training apparatus 100 can transmit the target food profile to the user, such that the user may selectively purchase a primary reinforcer for her dog based on the target food profile. Alternatively, the training apparatus 100 can automatically match the dog to a type of primary reinforcer based on the target food profile and suggest this type of primary reinforcer to the user.

In another variation, the training apparatus 100 can prompt the user to purchase a particular type of primary reinforcer based on her dog's motivation to eat particular types of primary reinforcer. For example, over time, the training apparatus 100 can determine, based on the video feed of the working field recorded during training sessions with the dog, that a dog exhibits increased motivation in response to receiving primary reinforcers of different textures. In this example, the training apparatus 100 can prompt the user to load the training apparatus 100 with a combination of a crunchy primary reinforcer and a soft primary reinforcer.

Alternatively, in another example, the training apparatus 100 can determine that a dog exhibits increased motivation in response to receiving soft treats but decreased motivation in response to receiving crunchy treats. In particular, in this example, the training apparatus 100 can initially prompt the user to load the training apparatus 100 with both crunchy and soft primary reinforcers. The training apparatus 100 can dispense both types of primary reinforcer (e.g., simultaneously, individually) and learn which type of primary reinforcer the dog prefers, such as based on: a duration between dispensation and consumption by the dog; which primary reinforcer the dog consumes first when dispensed simultaneously; quantity of each type of primary reinforcer consumed by the dog; etc. In this example, in response to identifying that the dog prefers the crunchy primary reinforcer, the training apparatus 100 can prompt the user to load the training apparatus 100 with only the crunchy primary reinforcer in order to increase the dog's motivation during training sessions. Additionally and/or alternatively, the training apparatus 100 can suggest to the user a type of primary reinforcer based on other food characteristics such as: texture; size; shape; caloric density; flavor; and/or any combination of these characteristics.

10. Analytics

The training apparatus 100 can track training session progress, caloric consumption, and physical characteristics of a dog during training sessions over time, record these data to the dog's profile, and adjust the dog's training schedule and/or feeding schedule based on these data.

In one implementation, the training apparatus 100 can collect images of the dog during each training session and extract features contained in these images to adjust the dog's feeding schedule. For example, the training apparatus 100 can: over a first period of time, serve a dog a first primary reinforcer during training sessions; collect images of the dog during training sessions over the first period of time; extract a set of dimensions of the dog from these images; estimate a weight of the dog based on the set of dimensions extracted from images; and, in response to estimating a high weight for the dog exceeding an expected weight based on the dog's breed and age, prompt the user to feed the dog a second primary reinforcer with a lower caloric density than the first primary reinforcer. Additionally and/or alternatively, the training apparatus 100 can prompt the user to feed the dog a third primary reinforcer with a higher caloric density in response to the dog's weight falling.

In a similar example, the training apparatus 100 can: track the dog's weight or visual size over time; track the caloric volume of units of a primary reinforcer dispensed to the dog during training sessions over this period of time; and update a schedule for training sessions and/or update the proportion of the total caloric consumption of the dog allocated to these training sessions based on these weight and Calorie data. For example, the training apparatus 100 can determine that a dog has exceeded a target weight gain or deviated from a target body shape (e.g., based on the dog's breed, age, or past body shape)—based on characteristics of the dog detected in video feeds recorded by the training apparatus 100 during training sessions involving the dog over time—and shorten durations of subsequent training sessions with the dog in order to decrease daily caloric intake of the dog. Conversely, if the training apparatus 100 determines that the dog has fallen below a target weight and/or deviated from its target body shape, the training apparatus 100 can: increase the duration of subsequent training sessions; increase a quantity of training repetitions (e.g., a number of "sit" commands issued and reinforced) scheduled for subsequent training session; and/or prompt the user to increase a quantity of food fed to the dog in order to increase the dog's daily caloric intake.

In another implementation, the training apparatus 100 processes images captured during a training session with a dog—such as in real-time—to confirm whether the dog consumed dispensed units; the training apparatus 100 can then access these consumption records and adjust a primary reinforcer or assign a different primary reinforcer to the dog accordingly. For example, the training apparatus 100 can: at a first time during a training session, dispense a first unit from a first primary reinforcer; access a ballistics model for the first primary reinforcer to calculate a location at which the first unit may have landed; at a second time during the training session, collect an image of a first region containing the first location; and, in response to detecting presence of the first unit within the first region, flag the first unit as rejected by the dog. At the end of the first week of training, the training apparatus 100 can tally a quantity of units flagged as rejected by the dog. If this quantity of units rejected by the dog during the last training session (or over a recent set of training sessions) exceeds a high threshold proportion (e.g., 40%) of units dispensed to the dog, the training apparatus 100 can prompt the user to switch to a second, higher-quality (e.g., higher-Calorie) primary reinforcer—that the dog may be more likely to consume—for future training sessions. Conversely, if this quantity of units rejected by the dog during the last training session (or over a recent set of training sessions) is less than a low threshold proportion (e.g., 1%) of units dispensed to the dog, the training apparatus 100 can prompt the user to switch to a third, lower-quality (e.g., lower-Calorie) primary reinforcer for future training sessions, which may enable the training apparatus 100 to reward the dog for more training cycles of various commands without increasing the quantity of Calories dispensed to the dog during these training sessions.

In one variation, the training apparatus 100 can update proportions of food fed to the dog manually by the user and automatically by the training apparatus 100. For example, in preparation for a difficult training session, the training apparatus 100 can calculate a lower proportion of food fed manually to the dog such as to increase a proportion of food fed automatically to the dog by the training apparatus 100. By allocating a higher proportion of food fed automatically to the dog by the training apparatus 100 than to food fed manually to the dog (e.g., by the user), the training apparatus 100 increases a quantity of units of the primary reinforcer that may be dispensed during a difficult training session, therefore increasing a number of opportunities for rewarding the dog during training.

In another example, the training apparatus 100 can initially prompt the user to load the training apparatus 100 with a first primary reinforcer characterized by a first caloric density. During subsequent training sessions with the user's dog, the training apparatus 100 can capture images of the dog, and the training apparatus 100 can derive or estimate the dog's weight and/or body shape from these images. After a training period of time (e.g., three months of training), in response to an estimated weight for the dog exceeding a target weight for the dog by more than a threshold deviance (e.g., 10%), the training apparatus 100 can: reduce the target caloric intake allocated to the dog; reduce the quantity of units from the first primary reinforcer allocated for dispensation to the dog by the training apparatus 100 during subsequent training sessions and thus reduce durations of the training sessions with the dog; maintain the quantity of food recommended to the user to feed to the dog (e.g., in order to minimize disruption to the user and to maintain greater control over caloric consumption by the dog); and recommend a second primary reinforcer with a second caloric density—less than the first caloric density of the first primary reinforcer—to the user. Once the training apparatus 100 determines that the second primary reinforcer has been loaded into the training apparatus 100, the training apparatus 100 can return to full-length training sessions with the full count of units allocated for dispensation to the dog by the training apparatus 100 during subsequent training sessions. Once the estimated weight of the dog returns to within a target weight range, the training apparatus 100 can prompt the user to reload the first primary reinforcer into the training apparatus 100 and reserve instructions to the user for properly feeding the dog outside of training sessions in order to maintain the dog's weight within the target range.

10.1 Updating the Health Profile

In one variation, as described above, the training apparatus 100 can characterize health of the dog over on a set of characteristics of the animal, such as: breed; age; sex; weight; size; shape; energy level; etc. The training apparatus 100 can continue to characterize the dog's health over time to track improvements and/or deteriorations of the dog's health. In this variation, the training apparatus 100 can leverage this characterization of the dog's health to inform: selection of types of primary reinforcer for training sessions; estimation of the target caloric intake; and/or selection of training protocols for execution during training sessions.

For example, during an initial period, the training apparatus 100 can prompt the user to input a breed, a sex, and an age of her dog. Based on this information, the training apparatus 100 can access a target health profile for the dog specifying a target weight, a target shape, and a target energy level. Then, during an initial training session, the training apparatus 100 can extract a first set of characteristics of the dog from a first video feed of the dog within a working field recorded by the training apparatus 100, the set of characteristics including a first weight, a first shape, and a first energy level of the dog. The training apparatus 100 can then characterize a first health profile for the dog based on the first set of characteristics extracted during the initial training session. Further, the training apparatus 100 can characterize a first difference between the target health profile and the first health profile of the dog. The training apparatus 100 can leverage this difference to estimate a first target caloric intake for the dog and inform selection a type of primary reinforcer for training sessions for the dog.

In this example, after a first training session succeeding the initial training session (e.g., one day later, one week later, one month later), the training apparatus 100 can extract a second set of characteristics—including a second weight, a second shape, and a second energy level—of the dog from a second video feed recorded during the first training session to characterize a second health profile for the dog. The training apparatus 100 can then characterize a second difference between the second health profile and the target health profile. Then, in response to the second difference falling below the first difference, the training apparatus 100 can confirm the first target caloric intake for the dog and/or any other training parameters (e.g., type of primary reinforcer, duration of training sessions, rigor of training sessions). Alternatively, the training apparatus 100 can adjust these parameters accordingly as this current health profile approaches the target health profile, such as to prevent overcorrection (e.g., excess weight loss). However, in response to the second difference exceeding the first difference, the training apparatus 100 can estimate a second target caloric intake for the dog and/or adjust other training parameters in order to promote improvement in the dog's health.

In one variation, the training apparatus 100 can generate and deliver (e.g., via native application executing on the user's mobile device) a report to the user including the health profile of the dog. Further, the training apparatus 100 can include suggestions for the user in the report such as: a type(s) of primary reinforcer to purchase; a schedule for manually feeding her dog (e.g., time of day, frequency, amount) outside of training sessions; a schedule for exercise for the dog outside of training sessions; etc.

11. Variation: Shared Training Apparatus

In one variation, the training apparatus 100 can be loaded with multiple types or configurations of primary reinforcers and can selectively dispense these primary reinforces during training sessions with various dogs, such as based on sizes, ages, and/or food motivation of these dogs. For example, the training apparatus 100 can: identify a first primary reinforcer loaded in the reservoir; access a first nutrient profile for the first primary reinforcer; and, based on the nutrient profile of the first primary reinforcer, load a first training protocol for a first training session. Then, during the first training session for a first dog, the training apparatus 100 can dispense units of the first primary reinforcer in response to detection of an action by the dog corresponding to a command output by the training apparatus 100. Later, in response to identifying the first primary reinforcer loaded in the reservoir, the training apparatus 100 can initiate a second training session for a second dog and repeat the first training protocol, the first training protocol corresponding to the first primary reinforcer. Alternatively, in response to identifying a second primary reinforcer loaded in the reservoir, the training apparatus 100 can access a second nutrient profile for the second primary reinforcer, and load a second training protocol based on the second nutrient profile. Then, the training apparatus 100 can initiate a second training session for the second dog according to the second training protocol, the second training protocol corresponding to the second primary reinforcer. Therefore, the training apparatus 100 can select and/or suggest primary reinforcers solely based on the selected training protocol, and without accessing a dog profile or receiving input by a user regarding the type of dog. Similarly, the training apparatus 100 can select and/or suggest training protocols solely based on a type primary reinforcer loaded in the reservoir.

In one variation, the training apparatus 100 can store dog profiles for multiple dogs and access these dog profiles in the presence of dogs to select and/or suggest primary reinforcers and training protocols. For example, the training apparatus 100 can identify a first dog (e.g., via scanning a tag on the dog's collar); load a first dog profile corresponding to the first dog; and, based on characteristics of the dog included in the dog profile (e.g., age, breed, size, reproductive status, previous training protocols completed) suggest a first primary reinforcer for loading in the reservoir. Then, in response to identifying the first primary reinforcer in the reservoir, the training apparatus 100 can load a first training protocol for the first dog and initiate a first training session. Then, at a later time, the training apparatus 100 can identify a second dog; load a second dog profile corresponding to the second dog; and, based on characteristics of the dog included in the dog profile, suggest a second primary reinforcer for loading in the reservoir. Then, in response to identifying the second primary reinforcer in the reservoir, the training apparatus 100 can load a second training protocol for the second dog and initiate a second training session. Additionally, the training apparatus 100 can store the first training session to the first dog profile and store the second training session to the second dog profile.

In another variation, the training apparatus 100 can identify a type of dog (e.g., breed, age, weight) in view of a video feed recorded near the training apparatus 100 and identify a particular primary reinforcer and/or training protocol based on the type of dog identified. For example, the training apparatus 100 can: record a video feed of a field near the training apparatus 100; detect a dog in the video feed; identify a breed, an age, and a weight of the dog based on images of the dog recorded in the video feed; suggest a first primary reinforcer based on the breed, the age, and the weight of the dog identified; and load a first training protocol based on the breed, the age, and the weight of the dog identified. Alternatively, the training apparatus 100 can load the first training protocol in response to confirming the first primary reinforcer was loaded in the reservoir of the training apparatus 100. In response to identifying a second primary reinforcer was loaded in the reservoir, the training apparatus 100 can load a second training protocol, based on the second primary reinforcer, the breed, the age, and the weight of the dog.

In another variation, the training apparatus 100 can identify a primary reinforcer based on a particular training session queued. For example, the training apparatus 100 can: load a first training protocol for a first training session; and identify a first primary reinforcer based on the first training protocol. Additionally and/or alternatively, the training apparatus 100 can: record a video feed of a field near the training apparatus 100; detect a dog in a video feed recorded near the training apparatus 100; identify characteristics (e.g., breed, age, weight) of the dog based on images of the dog recorded in the video feed; load a first training protocol based on these characteristics of the dog; and suggest a first primary reinforcer based on the first training protocol and characteristics of the dog.

12. Rejecting Food

In one variation, the training apparatus 100 can reject primary reinforcers if the primary reinforcer is unidentifiable by the training apparatus 100 (e.g., the SKU is not present in a remote database accessed by the training apparatus 100).

For example, the training apparatus 100 can: prompt the user to scan a SKU (or other identifier, such as an RFID tag, a barcode, a QR code, a unique alphanumeric sequence) present on a product packaging of a primary reinforcer; in response to the SKU not matching a SKU of a primary reinforcer in a set of primary reinforcers, reject this primary reinforcer (e.g., maintain locking of the reservoir); block initiation of the first training session; and prompt the user to load a different primary reinforcer. Alternatively, in response to the SKU not matching a SKU of a primary reinforcer in a set of primary reinforcers, the training apparatus 100 can prompt the user to manually input a set of characteristics of the primary reinforcer, such as caloric density, shape, and/or size. Alternatively, the training apparatus 100 can load a generic nutrient profile for the primary reinforcer.

In one variation, the training apparatus 100 can reject primary reinforcers for which an identifier (e.g., an RFID tag, a barcode, a QR code, a unique alphanumeric sequence) of product packaging containing the primary reinforcers was previously scanned at the training apparatus 100 or at the user's mobile device. For example, in response to the SKU matching a SKU of a previously scanned primary reinforcer, reject the primary reinforcer, block initiation of the first training session, and prompt the user to replace the loaded primary reinforcer with an alternate primary reinforcer before initiation the first training session.

In one variation, the training apparatus 100 can implement a counter to track a quantity of units of primary reinforcer available for dispensation, based on purchases of primary reinforcer by the user. For example, in response to a purchase by a user of a 500-unit bag of primary reinforcer, the training apparatus 100 can set the counter to 500 units of primary reinforcer available for dispensation. If the counter reaches zero, the training apparatus 100 can reject additional food loaded in the reservoir. Alternatively, in another example, if the counter reaches zero, the training apparatus 100 can issue a warning to the user to purchase another bag of primary reinforcer and enable dispensation of an additional quantity of primary reinforcer (e.g., 10, 20, enough for the next two training sessions).

In one variation, the training apparatus 100 can include a filter that limits flow of oversized (and undersized) treat units from the reservoir into the dispenser. For example, the training apparatus 100 can be loaded with a first filter configured to block units of a primary reinforcer that exhibit a size greater than a maximum size. Similarly, the training apparatus 100 can include a second filter configured to filter out units of primary reinforcer that exhibit a size less than a minimum size. In this example, the second filter can be installed in the bottom of the loader such that units exhibiting sizes smaller than the minimum size filter out the bottom of the loader and are not dispensed by the training apparatus 100.

In one variation, the training apparatus 100 can detect an excess of units of primary reinforcer (e.g., greater than one unit) loaded into the dispenser. For example, upon detecting multiple units of primary reinforces loaded in the dispenser, the training apparatus 100 can prompt an error message and/or request the user load a particular primary reinforcer.

The systems and methods described herein can be embodied and/or implemented at least in part as a training apparatus 100 configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a training apparatus 100 configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method comprising:
   at a first time:
      accessing a set of characteristics of an animal; and
      estimating a target caloric intake of the animal based on the set of characteristics;
   at a second time, identifying a type of primary reinforcer loaded into a training apparatus configured to dispense units of a primary reinforcer based on behaviors performed by the animal responsive to commands output by the training apparatus;
   in response to identifying the type of primary reinforcer as a first primary reinforcer, loading a first nutrient profile for the first primary reinforcer;
   in response to the first nutrient profile specifying a first caloric density of units of the first primary reinforcer, selecting a first training protocol for loading onto the training apparatus for a first training session for the animal based on the target caloric intake of the animal and the first caloric density of units of the first primary reinforcer; and
   in response to the first nutrient profile specifying a first size and a first shape of units of the first primary reinforcer, loading a first ballistics model corresponding to the first size and the first shape for dispensing units of the first primary reinforcer.

2. The method of claim 1, wherein selecting the first training protocol for loading onto the training apparatus for the first training session based on the target caloric intake and the first caloric density in response to the first nutrient profile specifying the first caloric density comprises:
   in response to the first nutrient profile specifying the first caloric density, calculating a target quantity of dispensations of units of the first primary reinforcer for the first training session based on the target caloric intake of the animal and the first caloric density of units of the first primary reinforcer; and
   loading the first training protocol for the first training session onto the training apparatus, the first training protocol specifying a first quantity of training instances corresponding to the target quantity of dispensations.

3. The method of claim 1, further comprising, during the first training session at the training apparatus:
- capturing a video feed of a working field near the training apparatus;
- detecting the animal in the video feed;
- outputting a command;
- detecting a first action of the animal in the video feed responsive to the command;
- characterizing a difference between the first action and a set of actions corresponding to the command; and
- in response to the difference falling below a threshold, dispensing a first unit of the first primary reinforcer into the field.

4. The method of claim 3, further comprising:
- during the first training session, tracking a caloric intake based on a quantity of units of the primary reinforcer dispensed by the training apparatus;
- calculating a first proportion of the target caloric intake of the animal consumed by the animal during the first training session; and
- prompting a user associated with the animal to feed the animal a second proportion of food based on a difference between the first proportion and the target caloric intake.

5. The method of claim 3:
- wherein accessing the set of characteristics of the animal comprises accessing the set of characteristics of a dog; and
- further comprising, during the first training session, in response to dispensing the first unit of the first primary reinforcer into the field:
  - detecting a first location of the first unit of the first primary reinforcer within the field based on the video feed;
  - detecting a second location of a mouth of the dog within the field based on the video feed; and
  - in response to detecting intersection of the first location and the second location, confirm consumption of the first unit of the first primary reinforcer by the dog.

6. The method of claim 1:
- wherein accessing the set of characteristics of the animal comprises accessing a breed and age of the animal; and
- wherein estimating the target caloric intake of the animal based on the set of characteristics comprises:
  - accessing a target health profile, in a set of target health profiles, corresponding to the breed and the age of the animal; and
  - estimating the target caloric intake of the animal based on the target health profile.

7. The method of claim 6:
- wherein accessing the set of characteristics of the animal comprises accessing the breed, the age, and the weight of the animal; and
- wherein estimating the target caloric intake of the animal based on the target health profile comprises:
  - interpreting a first health profile of the animal based on the breed, the age, and the weight of the animal;
  - characterizing a difference between the first target health profile and the first health profile of the animal; and
  - estimating the target caloric intake of the animal based on the difference.

8. The method of claim 1:
- wherein loading the first training protocol for the first training session onto the training apparatus in response to the first nutrient profile specifying the first caloric density of units of the first primary reinforcer comprises loading the first training protocol for the first training session onto the training apparatus in response to the first nutrient profile specifying the first caloric density of units of the first primary reinforcer, the first training protocol defining a first difficulty level; and
- further comprising:
  - in response to identifying the type of primary reinforcer as a second primary reinforcer, loading a second nutrient profile for the second primary reinforcer; and
  - in response to the second nutrient profile specifying a second caloric density of units of the second primary reinforcer, the second caloric density greater than the first caloric density, loading a second training protocol for the first training session for the animal onto the training apparatus based on the target caloric intake of the animal and the second caloric density of units of the second primary reinforcer, the second training protocol defining a second difficulty level greater than the first difficulty level.

9. A method comprising:
- during an initial period:
  - accessing a target caloric intake of an animal; and
  - in response to identifying a type of primary reinforcer loaded into a training apparatus as a first primary reinforcer, loading a first nutrient profile corresponding to the first primary specifying a first caloric density of units, a first size, and a first shape of units of the first primary reinforcer, loading a first ballistics model corresponding to the first size and the first shape for dispensing units of the first primary reinforcer, the training apparatus configured to dispense units of a primary reinforcer based on behaviors performed by an animal responsive to commands output by the training apparatus;
- during a first training session succeeding the initial period:
  - capturing a video feed of a working field near the training apparatus;
  - detecting the animal in the video feed;
  - outputting a first command;
  - detecting a first action of the animal;
  - characterizing a difference between the first action and a target action corresponding to the first command;
  - in response to the difference falling below a threshold difference, dispensing a first unit of the first primary reinforcer into the field; and
  - tracking a caloric intake of the animal based on a quantity of units of the first primary reinforcer dispensed by the training apparatus during the first training session and the first caloric density; and
- during a second period succeeding the first training session:
  - calculating a difference between the target caloric intake of the animal and the first caloric intake of the animal during the first training session;
  - accessing a second caloric density of units of food served to the animal by a user associated with the animal, units of food distinct from units of the first primary reinforcer;
  - calculating a remaining quantity of units of food for the animal based on the difference and the second caloric density; and
  - prompting the user to feed the animal the remaining quantity of units of food during the set period of time.

10. The method of claim 9, further comprising, during the initial period:
accessing a set of characteristics of the animal;
estimating the target caloric intake of the animal based on the set of characteristics; and
in response to the first nutrient profile specifying the first caloric density, loading a first training protocol for the first training session for the animal onto the training apparatus based on the target caloric intake of the animal and the first caloric density of units of the first primary reinforcer.

11. The method of claim 9:
wherein tracking the caloric intake of the animal during the first training session comprises, in response to dispensing the first unit of the first primary reinforcer into the field, updating the caloric intake of the animal based on the caloric density of the first unit of the first primary reinforcer.

12. The method of claim 9, further comprising, during the first training session, in response to the caloric intake exceeding a threshold caloric intake for the first training session, terminating the first training session.

13. The method of claim 12:
wherein terminating the first training session in response to the caloric intake exceeding the threshold caloric intake for the first training session comprises:
calculating the threshold caloric intake of the animal for the first training session based on the target caloric intake;
estimating a threshold quantity of units of the first primary reinforcer for dispensation during the first training session based on the first caloric density and the threshold caloric intake; and
in response to the quantity of the first primary reinforcer dispensed by the training apparatus exceeding the threshold quantity of units of the first primary reinforcer, terminating the first training session.

14. The method of claim 9:
wherein accessing the target caloric intake of the animal during the initial period comprises accessing the target caloric intake of the animal in response to identifying the animal at the training apparatus; and
further comprising:
during the initial period, in response to identifying a second animal at the training apparatus, accessing a second target caloric intake of the second animal; and
during a second training session, for the second animal, succeeding the initial period:
capturing a second video feed of the working field near the training apparatus configured to dispense units of the primary reinforcer based on behaviors performed by the second animal responsive to commands output by the training apparatus;
detecting the second animal in the video feed; and
tracking a second caloric intake of the second animal based on a second quantity of units of the first primary reinforcer dispensed by the training apparatus and the first caloric density.

15. A method comprising:
during an initial period:
accessing a target caloric intake of an animal;
identifying a type of primary reinforcer loaded into a training apparatus configured to dispense units of a primary reinforcer based on behaviors performed by the animal during a training session;
in response to identifying the type of primary reinforcer as a first primary reinforcer, loading a first nutrient profile for the first primary reinforcer;
in response to the first nutrient profile specifying a first caloric density of units of the first primary reinforcer, selecting a first training protocol for loading onto the training apparatus for execution during a first training session for the animal based on the target caloric intake and the first caloric density of units of the first primary reinforcer; and
in response to the first nutrient profile specifying a size and a shape of units of the first primary reinforcer, loading a ballistics model corresponding to the size and the shape for dispensation of units of the first primary reinforcer; and
during a first training session succeeding the initial period, dispensing units of the first primary reinforcer according to the first training protocol and the ballistics model.

16. The method of claim 15:
wherein accessing the target caloric intake of the animal comprises:
accessing a set of characteristics of the animal; and
estimating the target caloric intake of the animal based on the set of characteristics;
wherein dispensing units of the first primary reinforcer according to the first training protocol during the first training session comprises, during the first training session:
capturing a video feed of a working field near the training apparatus;
detecting the animal in the video feed;
outputting a command according to the first training protocol;
detecting a first action of the animal in the video feed responsive to the command;
characterizing a difference between the first action and a set of actions corresponding to the command; and
in response to the difference falling below a threshold, dispensing a first unit of the first primary reinforcer into the field.

17. The method of claim 15, further comprising:
during the first training session, tracking a caloric intake of the animal based on a quantity of units of the primary reinforcer dispensed by the training apparatus; and
during second period succeeding the first training session:
calculating a first proportion of the target caloric intake consumed by the animal during the first training session; and
prompting a user associated with the animal to feed the animal a second proportion of food based on a difference between the first proportion and the target caloric intake.

18. The method of claim 15:
wherein accessing a target caloric intake of an animal comprises:
accessing a first set of characteristics of an animal;
characterizing a first health profile of the animal based on the first set of characteristics; and
estimating a first target caloric intake of the animal based on the first health profile; and
further comprising, during a second period succeeding the first training session:
accessing a second set of characteristics of the animal;
characterizing a second health profile of the animal based on the second set of characteristics; and estimating a second target caloric intake of the animal based on the first health profile and the second health profile.

19. The method of claim 18:
wherein accessing the first set of characteristics comprises accessing a breed, a first age, and a first weight of the animal;
wherein characterizing the first health profile of the animal based on the first set of characteristics comprises characterizing the first health profile of the animal based on the breed, the first age, and the first weight of the animal;
wherein accessing the second set of characteristics of the animal comprises accessing the breed, a second age, and a second weight of the animal;
wherein characterizing the second health profile of the animal based on the second set of characteristics comprises characterizing the second health profile of the animal based on the breed, the second age, and the second weight;
further comprising, characterizing a difference between the first weight and the second weight; and
wherein estimating the second target caloric intake of the animal based on the first health profile and the second health profile comprises estimating the second caloric target caloric intake of the animal based on the difference.

* * * * *